United States Patent [19]

Hamprecht et al.

[11] Patent Number: 4,523,942

[45] Date of Patent: Jun. 18, 1985

[54] 4H-3,1-BENZOXAZINE DERIVATIVES, COMPOSITIONS AND HERBICIDAL USE

[75] Inventors: Gerhard Hamprecht, Weinheim; Juergen Varwig, Heidelberg; Bruno Wuerzer, Otterstadt, all of Fed. Rep. of Germany

[73] Assignee: BASF Aktiengesellschaft, Fed. Rep. of Germany

[21] Appl. No.: 462,477

[22] Filed: Jan. 31, 1983

Related U.S. Application Data

[63] Continuation of Ser. No. 217,560, Dec. 17, 1980, abandoned.

[30] Foreign Application Priority Data

Jan. 5, 1980 [DE] Fed. Rep. of Germany ....... 3000309

[51] Int. Cl.³ ............... A01N 43/86; C07D 265/20; C07D 265/22
[52] U.S. Cl. .......................... 71/88; 544/92; 71/90
[58] Field of Search ............... 544/92; 71/88

[56] References Cited

U.S. PATENT DOCUMENTS 3,357,977 12/1967 Eurrede ..................... 544/92
3,970,652 7/1976 Doyle ........................ 544/92
4,315,766 2/1982 Hamprecht et al. ........... 544/92

*Primary Examiner*—Robert W. Ramsuer
*Attorney, Agent, or Firm*—Keil & Weinkauf

[57] ABSTRACT

Novel 4H-3,1-benzoxazine derivatives of the formula

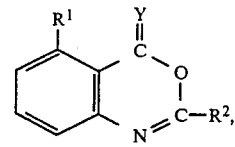

where $R^1$, $R^2$ and Y have the meanings given in the disclosure, a process for their preparation, and their use for combating unwanted plant growth.

14 Claims, No Drawings

4H-3,1-BENZOXAZINE DERIVATIVES, COMPOSITIONS AND HERBICIDAL USE

This is a continuation of application Ser. No. 217,560, filed Dec. 17, 1980, now abandoned.

The present invention relates to substituted 4H-3,1-benzoxazine derivatives, a process for their preparation, herbicides which contain these compounds as active ingredients, and a process for controlling undesired plant growth by means of these compounds.

4H-3,1-Benzoxazin-4-ones have been disclosed as intermediates for the synthesis of pharmacologically active compounds (German Laid-Open Applications DOS No. 1,670,375 and DOS No. 2,556,590), and as active ingredients of herbicides (Belgian Pat. No. 648,259 and U.S. Pat. No. 3,970,652). In particular, 4H-3,1-benzoxazin-4-ones which carry a trifluoromethyl-substituted phenyl radical in the 2-position act as herbicides and possess a higher activity, and a broader action spectrum, than unsubstituted 2-phenyl-4H-3,1-benzoxazin-4-one. However, these compounds have little effect on Amaranthaceae and undesired species of Leguminosae.

Further, German Pat. No. 1,542,836 has disclosed that 3-isopropyl-2,1,3-benzothiadiazin-4-one 2,2-dioxide (Bentazon) acts as a herbicide.

We have found that 4H-3,1-benzoxazine derivatives of the formula I

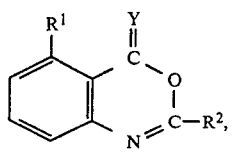

where $R^1$ is hydrogen, halogen, nitro, alkyl, haloalkyl, haloalkoxy or haloalkylmercapto each of 1 to 4 carbon atoms, cyano, thiocyanato,

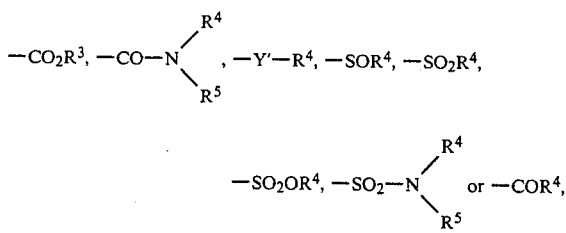

where $R^3$ is alkyl or alkenyl of up to 4 carbon atoms,
$R^4$ is alkyl of 1 to 4 carbon atoms,
$R^5$ is hydrogen or alkyl of 1 to 4 carbon atoms and
$Y'$ is oxygen or sulfur,
$Y$ is oxygen or sulfur and
$R^2$ is phenyl which is monosubstituted or disubstituted by haloalkenyl, haloalkenyloxy or haloalkenylmercapto, each of up to 3 carbon atoms, or by

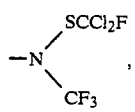

the substituents in the case of disubstitution being identical or different, or is thienyl, thenyl or thienylethenyl which are substituted by chlorine, methyl or trifluoromethyl, or is 1,2,3-, 1,2,5- or 1,3,4-thiadiazole which are unsubstituted or substituted by chlorine or trifluoromethyl, or is 5-methyl-1,2,3-thiadiazole, and if $R^1$ is hydrogen or halogen, $R^2$ may also be phenyl which is monosubstituted by haloalkyl of up to 3 carbon atoms, with the exception of trifluoromethyl, or by trifluoroacetyl, if $R^1$ is not hydrogen, $R^2$ may also be thienyl, 1,2,3-, 1,2,5- or 1,3,4-thiadiazole which are unsubstituted or methyl-substituted, or phenyl which is monosubstituted by alkylmercapto, alkylsulfonyl, haloalkylsulfinyl or haloalkylsulfonyl, each of up to 3 carbon atoms, if $R^1$ is halogen, $R^2$ may also be phenyl which is monosubstituted or disubstituted by haloalkyl of up to 3 carbon atoms, the substituents in the case of disubstitution being identical or different, and if $R^1$ is neither hydrogen nor halogen, $R^2$ may also be phenyl monosubstituted by alkylsulfinyl or haloalkylmercapto, each of up to 3 carbon atoms, are well tolerated by a range of crops, and are more active herbicides and possess a broader action spectrum than known 4H-3,1-benzoxazine derivatives.

Examples of $R^1$ in formula I are hydrogen, fluorine, chlorine, bromine, iodine, nitro, methyl, ethyl, isopropyl, n-propyl, n-butyl, isobutyl, tert.-butyl, trichloromethyl, difluorochloromethyl, trifluoromethyl, difluoromethyl, 2,2,1,1-tetrafluoroethyl, trifluoromethoxy, hexafluoroisopropoxy, difluoromethylmercapto, trifluoromethylmercapto, haloalkoxy or haloalkylmercapto of the formula $Y''-CF_2C(Z)_3$, where $Y''$ is oxygen or sulfur and each Z, independently of the others, is hydrogen, fluorine, chlorine, bromine or iodine, eg. 2,2,1,1-tetrafluoroethoxy, 1,1-difluoroethoxy, 2,2,1,1-tetrafluoroethylmercapto and 1,1-difluoroethylmercapto, cyano, thiocyanato, $CO_2CH_3$, $CO_2C_2H_5$, $CO_2$—$CH(CH_3)_2$, $CO_2$—$CH_2$—$CH$=$CH_2$, $CO$—$N(CH_3)_2$, $CO$—$N(C_2H_5)_2$, methoxy, ethoxy, n-butoxy, isobutoxy, methylthio, ethylthio, n-propylthio, sec.-butylthio, $SOCH_3$, $SOC_2H_5$, $SO_2CH_3$, $SO_2C_2H_5$, $SO_2C_3H_7$, $SO_2OCH_3$, $SO_2OC_2H_5$, $SO_2OC_4H_9$, $SO_2NHCH_3$, $SO_2N(CH_3)_2$, $SO_2N(C_2H_5)_2$, formyl, acetyl and propionyl.

Examples of $R^2$ in formula I are 2-(thien-2-yl)ethenyl, 2-(thien-3-yl)-ethenyl, 4-chloro-1,2,3-thiadiazol-5-yl, 4-trifluoromethyl-1,2,3-thiadiazol-5-yl, 3-chloro-1,2,5-thiadiazol-4-yl, 3-trifluoromethyl-1,2,5-thiadiazol-4-yl, 2-chloro-1,3,4-thiadiazol-5-yl, 2-trifluoromethyl-1,3,4-thiadiazol-5-yl, 4-methyl-1,2,3-thiadiazol-5-yl, 5-chloro-1,2,3-thiadiazol-4-yl, 5-trifluoromethyl-1,2,3-thiadiazol-4-yl, 5-methyl-1,2,3-thiadiazol-4-yl, 3-methyl-1,2,5-thiadiazol-4-yl, 2-methyl-1,3,4-thiadiazol-5-yl, thien-2-yl, thien-3-yl, 2-methyl-thien-5-yl, 2-methyl-thien-4-yl, 2-methyl-thien-3-yl, 3-methyl-thien-5-yl, 3-methyl-thien-4-yl, 3-methyl-thien-2-yl, 2-chloro-thien-5-yl, 2-chloro-thien-4-yl, 2-chloro-thien-3-yl, 3-chloro-thien-5-yl, 3-chloro-thien-4-yl, 3-chloro-thien-2-yl, 2-trifluoromethyl-thien-2-yl, 2-trifluoromethyl-thien-4-yl, then-2-yl, 1,2,3-thiadiazol-4-yl, 1,2,3-thiadiazol-5-yl, 1,2,5-thiadiazol-3-yl, 1,3,4-thiadiazol-2-yl or a phenyl radical, which may carry the following substituents: chloromethyl, dichloromethyl, trichloromethyl, fluoromethyl, difluoromethyl, trifluoromethyl, chlorofluoromethyl, chlorodifluoromethyl, dichlorofluoromethyl, 1,1-difluoroethyl, pentafluoroethyl, 2,3,3-trichloroallyl, trifluoroacetyl, 1,2-dichlorovinyloxy, trichlorovinyloxy, 1,2-difluorovinyloxy, 2-chloro-1,2- difluorovinyloxy, 1-fluoro-2,2-dichlorovinyloxy, 2,2-dichlorovinyloxy, 2,2-dibromovinyl, 2-chlorovinyloxy, 2-chloro-prop-1-enyloxy, 1,2-dichlorovinylmercapto, trichlorovinylmercapto, 1,2-difluorovinylmercapto, 2-chloro-1,2-difluorovinylmercapto, 2,2-dichlorovinylmercapto, 2-chlorovinylmercapto, methylmercapto, ethylmercapto, difluoromethylmercapto, trifluoromethylmercapto, 1,1-difluoroethylmercapto, 2,2,1,1-tetrafluoroethylmercapto, $SOCH_3$, $SOC_2H_5$, $SO_2CH_3$, $SO_2C_2H_5$, $SO_2C_3H_7$, $SOCF_3$, $SOCF_2Cl$, $SO_2CF_3$ and $SO_2CF_2Cl$.

Preferred compounds of the formula I are those where Y is oxygen, $R^1$ is hydrogen and $R^2$ is phenyl which is monosubstituted by haloalkyl or haloalkenyl, each of up to 3 carbon atoms, with the exception of trifluoromethyl, and those in which Y is oxygen, $R^1$ is halogen and $R^2$ is phenyl which is monosubstituted by haloalkyl of up to 3 carbon atoms, especially trifluoromethyl, or by alkylmercapto, alkylsulfonyl, haloalkylsulfinyl or haloalkylsulfonyl, each of up to 3 carbon atoms.

The 4H-3,1-benzoxazine derivatives of the formula I are obtained by reacting an unsubstituted or substituted anthranilic acid of the formula II.

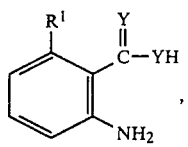

where $R^1$ and Y have the above meanings, with at least two moles of a carboxylic acid halide of the formula III

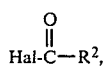

where $R^2$ has the above meanings and Hal is halogen, especially fluorine, chlorine or bromine, in an aromatic tertiary amine as the solvent, at from 10° to 60° C.

If anthranilic acid and 3-(1,2-dichlorovinyloxy)benzoyl chloride are used as starting materials, the course of the reaction can be represented by the following equation:

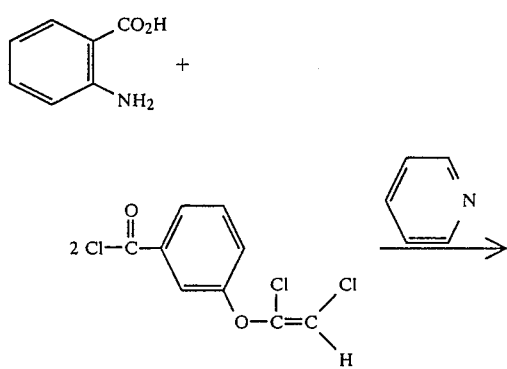

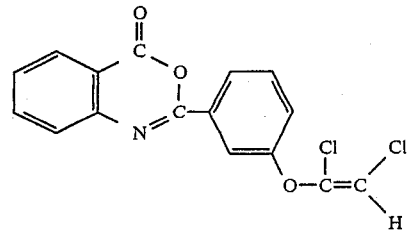

Advantageously, a one-fold excess of the carboxylic acid halide of the formula III is run into a solution of the anthranilic acid of the formula II in 5–25 moles, per mole of anthranilic acid, of an aromatic amine, at from 10° to 60° C., and the mixture is then stirred for 30 minutes at 25° C. (J.Chem.Soc. (C) 1968, 1593). To work up the mixture, ice water is then stirred into it, and the precipitate formed is filtered off. Alternatively, the reaction may be carried out in the reverse manner, by adding the anthranilic acid to the carboxylic acid halide of the formula III.

Examples of suitable aromatic tertiary amines are pyridine, α-, β- and γ-picoline, lutidine, quinoline and acridine.

The benzoxazine derivatives of the formula I may also be obtained by reacting an unsubstituted or substituted anthranilic acid of the formula II

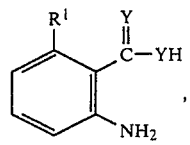

where $R^1$ and Y have the above meanings, or an alkali metal salt or alkaline earth metal salt of this anthranilic acid, with about the stoichiometric amount of a carboxylic acid halide of the formula III

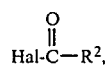

where $R^2$ has the above meanings and Hal is halogen, in an inert organic solvent or in water, in the presence or absence of an acid acceptor, at from 0° to 60° C., to give a carboxamide of the formula IV

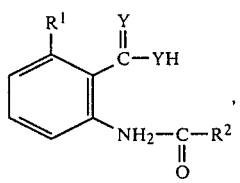

where $R^1$, $R^2$ and Y have the above meanings, and then cyclizing this compound in the presence of a dehydrating agent at from 30° to 150° C.

If 2-methyl-thiophene-4-carboxylic acid chloride and anthranilic acid are used as starting materials, the course of the reaction may be represented by the following equation:

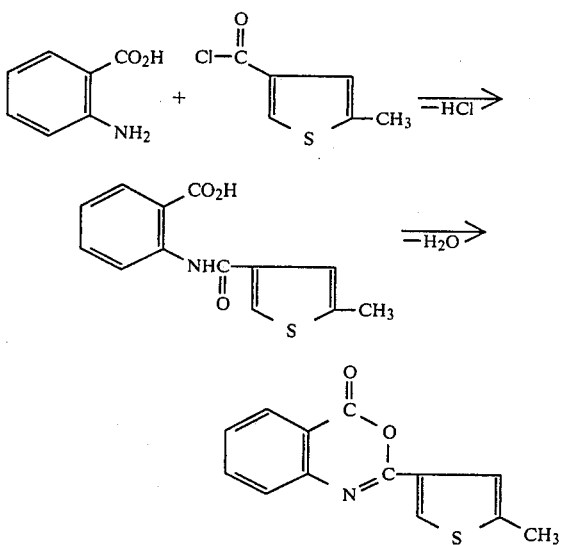

Suitable inert solvents for this reaction are hydrocarbons, eg. naphtha, gasoline, toluene, pentane, hexane, cyclohexane and petroleum ether, halohydrocarbons, eg. methylene chloride, chloroform, carbon tetrachloride, 1,1- and 1,2-dichloroethane, 1,1,1- and 1,1,2-trichloroethane, chlorobenzene, o-, m- and p-dichlorobenzene and o-, m- and p-chlorotoluene, nitrohydrocarbons, eg. nitrobenzene, nitroethane and o-, m- and p-chloronitrobenzene, nitriles, eg. acetonitrile, butyronitrile and isobutyronitrile, ethers, eg. diethyl ether, di-n-propyl ether, tetrahydrofuran and dioxane, esters, eg. ethyl acetoacetate, ethyl acetate and isobutyl acetate, and amides, eg. formamide, methylformamide and dimethylformamide.

All conventional acid-binding agents may be used as acid acceptors. Amongst these, alkali metal hydroxides, alkali metal carbonates and tertiary organic bases are preferred. Examples of particularly suitable acceptors are sodium hydroxide, sodium carbonate, sodium bicarbonate, triethylamine, pyridine, trimethylamine, α-, β- and γ-picoline, lutidine, N,N-dimethylaniline, N,N-dimethylcyclohexylamine, quinoline, tri-n-propylamine and tri-n-butylamine. The acid-binding agent is advantageously employed in equivalent amount to the carboxylic acid halide of the formula III.

Suitable dehydrating agents include symmetrical and mixed carboxylic acid anhydrides, eg. acetic anhydride, propionic anhydride, butyric anhydride, formic-acetic anhydride, formic-propionic anhydride and aceto-propionic anhydride, as well as dicyclohexylcarbodiimide and thionyl chloride. The cyclization is carried out in the presence of from 1 to 10 moles of dehydrating agent per mole of carboxamide of the formula IV.

In this process the starting materials of the formulae II and III are employed in about the stoichiometric ratio, ie. advantageously using from 0.9 to 1.1 moles of starting material of the formula III per mole of starting material of the formula II.

The process is advantageously carried out by running the carboxylic acid halide of the formula III and the equivalent amount of acid acceptor, through two separate inlets, into about the equivalent amount of the anthranilic acid of the formula II, or of a salt thereof, in an inert organic solvent or in water, at from 0° to 60° C. The reaction mixture is then stirred for 15 minutes at room temperature, and is concentrated if appropriate; it is then acidified with 5N hydrochloric acid whilst warm, and after cooling, the product is filtered off (J.Org.Chem. 2 (1944), 396), giving an N-acyl-2-aminobenzoic acid. The latter can then be cyclized to the desired 4H-3,1-benzoxazine in the presence of 5 to 10 moles, per mole of product, of a carboxylic acid anhydride, eg. acetic anhydride, as the dehydating agent, by stirring at from 30° to 150° C., where appropriate whilst distilling off the acetic acid formed. To work up the mixture, excess dehydrating agent is removed under reduced pressure and the product is purified by recrystallization, if necessary. It is also possible to employ the converse procedure and run the anthranilic acid into the carboxylic acid halide. If dicyclohexylcarbodiimide or thionyl chloride are used as dehydrating agent, the cyclization can be carried out using only from 1 to 4 moles thereof per mole of product.

4H-3,1-Benzoxazines of the formula I, where $R^2$ is phenyl substituted by haloalkenyloxy or haloalkenylmercapto, are advantageously prepared by converting the haloalkenyloxy-substituted or haloalkenylmercapto-substituted benzoic acid to the corresponding acid chloride (Houben-Weyl, Methoden der organischen Chemie, Volume 8, page 463 et seq., 4th Edition, Georg Thieme-Verlag, Stuttgart 1952) and then converting this compound, in a conventional manner, to the corresponding amide with an unsubstituted or substituted anthranilic acid of the formula II. The amide can then be converted to the substituted 2-phenyl-3,1-benzoxazine derivative by cyclizing in the presence of a dehydrating agent.

The 4H-3,1-benzoxazine derivatives of the formula I may be isolated from the reaction mixture by treating the latter with water, dilute alkali or dilute acid to remove by-products and unconverted anthranilic acid, acid chloride or base hydrochloride, and then drying and concentrating it. Where required, the end product may also be purified by recrystallization or chromatography.

The preparation of 3-(1',2'-dichlorovinyloxy)benzoyl chloride will now be described as an example of the preparation of a carboxylic acid halide of the formula III:

(a) 185 parts of trichloroethylene are introduced into a suspension of 180 parts of the sodium salt of methyl 3-hydroxybenzoate in 200 parts of ethylene glycol monoethyl ether in an autoclave, and the mixture is stirred for 2 hours at 150° C. The solvent is then stripped off under reduced pressure, the viscous residue is taken up in 300 parts of methylene chloride and the solution is filtered in the presence of active charcoal and is chromatographed over neutral alumina. After removing the methylene chloride under reduced pressure from the whole eluate, the residue is distilled through a Vigreux column at 125°–131° C./0.6 mbar, giving methyl 3-(1',2'-dichlorovinyloxy)-benzoate, of $n_D^{25} = 1.5419$.

(b) 30 parts of the ester obtained above, in a solution of 7.2 parts of potassium hydroxide in 100 parts of water and 9 parts of ethanol, are stirred for 2 hours under reflux. The reaction mixture is then extracted once with 50 parts of ether, after which it is stirred into 70 parts by volume of ice-cold 12% strength hydrochloric acid, and the product is filtered off and washed with water. After drying, 24 parts of 3-(1',2'-dichlorovinyloxy)-benzoic acid, of melting point 137°–141° C., are obtained.

(c) 48 parts of thionyl chloride and one drop of pyridine are added to 81.6 parts of 3-(1',2'-dichlorovinyloxy)-benzoic acid in 620 parts of 1,2-dichloroethane and the mixture is stirred for 3 hours under reflux. It is then concentrated under reduced pressure and 85 parts of 3-(1',2'-dichlorovinyloxy)-benzoyl chloride of melting point 50°-54° C. are isolated.

The Examples which follow illustrate the preparation of the novel 4H-3,1-benzoxazine derivatives of the formula I. Parts by weight bear the same relation to parts by volume as that of the kilogram to the liter.

EXAMPLE 1

Preparation of 2-(3'-trifluoromethylphenyl)-5-chloro-4H-3,1-benzoxazin-4-one (a) 23 parts of 3-trifluoromethylbenzoyl fluoride and 12.2 parts of triethylamine are introduced simultaneously, through 2 separate inlets, into a solution of 20.6 parts of 6-chloroanthranilic acid in 310 parts of 1,2-dichloroethane at 20°-25° C., and the mixture is then stirred for 10 minutes. Thereafter it is extracted once with 70 parts by volume of 1N hydrochloric acid, whereupon a colorless precipitate separates out in both phases. The precipitate is separated and dissolved in ethyl acetate, and the organic phase is washed with 1N hydrochloric acid and with water, dried over magnesium sulfate and concentrated; this gives 32 parts of N-3'-trifluoromethylbenzoyl-6-chloroanthranilic acid, of melting point 217°-219° C. The same procedure, i.e. washing with 1N hydrochloric acid and with water, drying over magnesium sulfate and concentrating, is followed with the 1,2-dichloroethane phase previously obtained, giving a further 7 parts of the same product, of melting point 210°-218° C.

(b) 25 parts of N-3'-trifluoromethylbenzoyl-6-chloroanthranilic acid in 250 parts of acetic anhydride are stirred under reflux for two and a half hours. The mixture is then concentrated under reduced pressure, the residue is taken up in methylene chloride and this solution is washed with 0.5N sodium hydroxide solution, using 100 parts by volume each time, and then with water, and is dried. Thereafter the solution is chromatographed over neutral alumina, and 23 parts of 2-(3'-trifluoromethylphenyl)-5-chloro-4H-3,1-benzoxazin-4-one, of melting point 116°-120° C., are obtained. Yield: 97% of theory.

EXAMPLE 2

Preparation of 2-(3'-trifluoromethylphenyl)-5-fluoro-4H-3,1-benzoxazin-4-one (a) 23 parts of 3-trifluoromethylbenzoyl fluoride and 15.3 g of dimethylcyclohexylamine are introduced simultaneously, through two separate inlets, into a solution of 18.6 parts of 6-fluoroanthranilic acid in 350 parts of ethyl acetate at 25°-30° C. The reaction mixture is stirred for a further 30 minutes and is extracted once with 1N hydrochloric acid and then with water. It is then dried and concentrated, giving 38 parts of N-3'-trifluoromethylbenzoyl-6-fluoroanthanilic acid of melting point 183°-185° C.; yield: 97% of theory.

(b) 25 parts of thionyl chloride are added to a suspension of 23 parts of N-3'-trifluoromethylbenzoyl-6-fluoroanthranilic acid in 150 parts of 1,2-dichloroethane at room temperature, and the reaction mixture is then stirred for one hour under reflux. Thereafter it is concentrated, the residue is taken up in methylene chloride and this solution is extracted once with water and twice with 0.5N sodium hydroxide solution, using 100 parts by volume each time. After drying, concentrating, filtering off and washing with a small amount of cyclohexane, 20 parts of 2-(3'-trifluoromethylphenyl)-5-fluoro-4H-3,1-benzoxazin-4-one, of melting point 115°-121° C., are obtained; yield: 92% of theory.

The following 4H-3,1-benzoxazine derivatives of the formula I may be prepared by corresponding processes:

$$\text{structure with Y=C, O, N, C-R}^2$$

| No. | R² | Y | M.p. [°C.] |
|---|---|---|---|
| 3 | phenyl-CF₂H | O | |
| 4 | phenyl-CF₂Cl | O | 106–108 |
| 5 | phenyl-CFCl₂ | O | 92–95 |
| 6 | phenyl-CF₂H | S | |
| 7 | phenyl-CF₂Cl | O | |
| 8 | phenyl-CF₂H | O | |
| 9 | phenyl-CF₂Cl | S | |
| 10 | phenyl-CF₂CF₃ | O | |

-continued
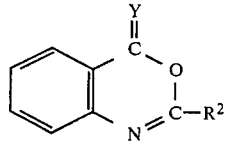
| | | Y | |
|---|---|---|---|
| 11 | 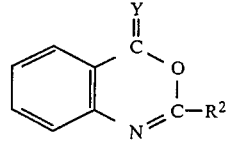 | O | |
| 12 | 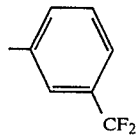 | O | |
| 13 | 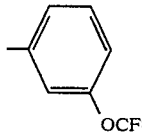 | O | |
| 14 | 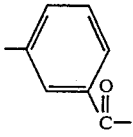 | O | 109–112 |
| 15 | 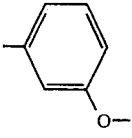 | O | |
| 16 | 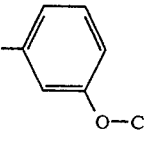 | S | |
| 17 | 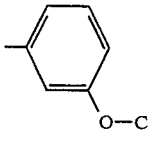 | O | |
| 18 | 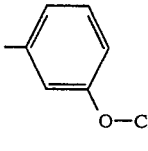 | O | |
| 19 | 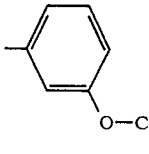 | O | |
-continued
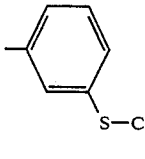
| | | Y | |
|---|---|---|---|
| 20 | 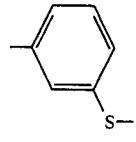 | O | |
| 21 | 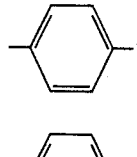 | O | |
| 22 | 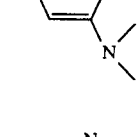 | O | 97–101 |
| 23 | 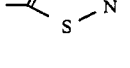 | O | |
| 24 | 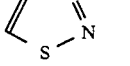 | O | 182–185 |
| 25 | 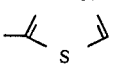 | O | |
| 26 | 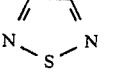 | O | |
| 27 | 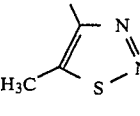 | O | |
| 28 | 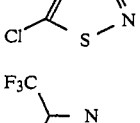 | S | |
| 29 | 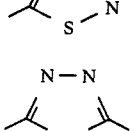 | O | |
| 30 | 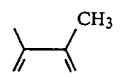 | O | |
| 31 | 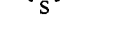 | O | |

4,523,942
-continued
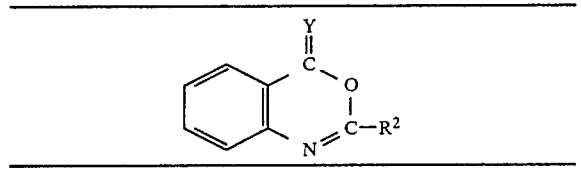
| No. | R² | Y | M.p. [°C.] |
|---|---|---|---|
| 32 | 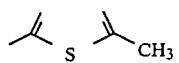 | O | |
| 33 | 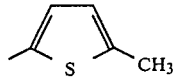 | O | 155–157 |
| 34 | 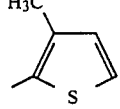 | O | 117–120 |
| 35 | 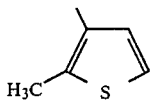 | O | |
| 36 | 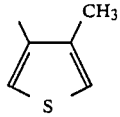 | O | |
| 37 | 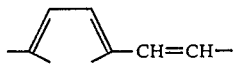 | O | 150–154 |
| 38 | 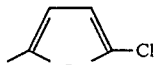 | O | 160–163 |
| 39 | 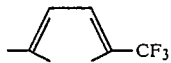 | O | |
| 40 | 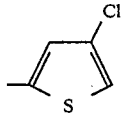 | O | |
| 41 |  | O | |
| 42 | 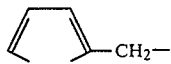 | O | 89–92 |
| No. | R¹ | R² | Y | M.p. [°C.] |
|---|---|---|---|---|
| 43 | F | 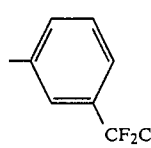 | O | |
-continued
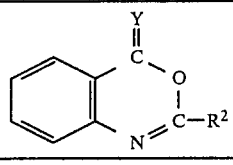
| No. | R¹ | R² | Y | M.p. [°C.] |
|---|---|---|---|---|
| 44 | Br | 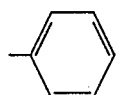 | O | |
| 45 | I | 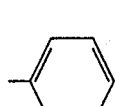 | O | |
| 46 | CH₃ | 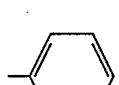 | O | |
| 47 | CF₃ | 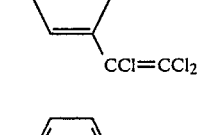 | S | |
| 48 | Cl | 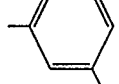 | O | 144–147 |
| 49 | Cl |  | O | 222–228 |
| 50 | Cl | 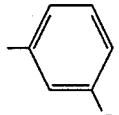 | O | 148–150 |
| 51 | Cl |  | O | 106–108 |
| 52 | F | 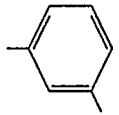 | O | 136–139 |
| 53 | Cl |  | O | |

| # | Y | R² | X | m.p. |
|---|---|---|---|---|
| 54 | Cl | 3-(SOCF₃)-C₆H₄- | O | |
| 55 | CN | 3-(OCCl=CCl₂)-C₆H₄- | O | |
| 56 | CO₂CH₃ | 3-(O-CCl=CHCl)-C₆H₄- | O | |
| 57 | SOCH₃ | 3-(O-CCl=CHCl)-C₆H₄- | S | |
| 58 | Cl | 3-(SO₂CF₃)-C₆H₄- | O | |
| 59 | Cl | 3-(SOCF₂Cl)-C₆H₄- | O | |
| 60 | Cl | 3-(SO₂CF₂Cl)-C₆H₄- | O | |
| 61 | Cl | 3-(CFCl₂)-C₆H₄- | | 138–140 |
| 62 | CH₃—CO | 3-(O-CCl=CHCl)-C₆H₄- | O | |
| 63 | NO₂ | 3-(SCF₃)-C₆H₄- | O | 131–134 |
| 64 | Cl | 3-(CHF₂)-C₆H₄- | O | 117–119 |
| 65 | Cl | -CH₂-(2-thienyl) | O | |
| 66 | Cl | 5-methyl-2-thienyl | O | 176–178 |
| 67 | Cl | 2,5-dimethyl-3-thienyl | O | 189–192 |
| 68 | Cl | 3-methyl-2-thienyl (H₃C) | O | 155–158 |
| 69 | F | 5-methyl-2-thienyl | O | 183–186 |
| 70 | Cl | 4,5-dimethyl-1,2,3-thiadiazol-yl | O | |
| 71 | F | 4,5-dimethyl-1,2,3-thiadiazol-yl | O | |
| 72 | Cl | 1,2,3-thiadiazol-4-yl | O | 238–243 |
| 73 | Cl | 3-(CF₂Cl)-C₆H₄- | O | 96–100 |

| # | | | | |
|---|---|---|---|---|
| 74 | Br | –⟨C₆H₄⟩–CH₂F | S | |
| 75 | Cl | –⟨C₆H₄⟩–O–CCl=CHCl | O | 119–123 |
| 76 | F | –⟨C₆H₄⟩–O–CCl=CCl₂ | O | |
| 77 | Cl | –⟨C₆H₄⟩–O–CH=CHCl | O | |
| 78 | Cl | –⟨C₆H₄⟩–S–CCl=CHCl | O | |
| 79 | Cl | –⟨C₆H₄⟩–C(=O)–CF₃ | O | |
| 80 | F | –⟨C₆H₄⟩–CF₃ (ortho) | O | 94–98 |
| 81 | NO₂ | –⟨C₆H₄⟩–SCH₃ | O | |
| 82 | CH₃ | –⟨C₆H₄⟩–SCH₃ | S | |
| 83 | CH₃ | –⟨C₆H₄⟩–SO₂CH₃ | O | |
| 84 | CH₃ | –⟨C₆H₄⟩–SOCF₃ | O | |
| 85 | NO₂ | –⟨C₆H₄⟩–SOCF₃ | O | |
| 86 | NO₂ | –⟨C₆H₄⟩–SO₂CF₃ | O | |
| 87 | F | –⟨C₆H₄⟩–CF₂Cl | O | 129–133 |
| 88 | Cl | –⟨C₆H₄⟩–CHCl₂ | O | 180–183 |

The active ingredients according to the invention may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient.

Examples of formulations are given below.

I. 90 parts by weight of the compound of Example 1 is mixed with 10 parts by weight of N-methyl-α-pyrrolidone. A mixture is obtained which is suitable for application in the form of very fine drops.

II. 20 parts by weight of the compound of Example 2 is dissolved in a mixture consisting of 80 parts by weight of xylene, 10 parts by weight of the adduct of 8 to 10 moles of ethylene oxide with 1 mole of oleic acid-N-monoethanolamide, 5 parts by weight of the calcium salt of dodecylbenzenesulfonic acid, and 5 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

III. 20 parts by weight of compound no. 14 is disloved in a mixture consisting of 40 parts by weight of cyclohexanone, 30 parts by weight of isobutanol, 20 parts by weight of the adduct of 7 moles of ethylene oxide with 1 mole of isooctylphenol, and 10 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound no. 33 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 20 parts by weight of compound no. 69 is well mixed with 3 parts by weight of the sodium salt of diisobutylnaphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

VI. 3 parts by weight of compound no. 37 is intimately mixed with 97 parts by weight of particulate kaolin. A dust is obtained containing 3% by weight of the active ingredient.

VII. 30 parts by weight of compound no. 66 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 20 parts of compound no. 72 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients or agents may be applied pre- or post-emergence, i.e., before unwanted plants have germinated from seed or sprouted from vegetative plants parts, or to the leaves of unwanted and crop plants. Preferably, the new active ingredients are applied after emergence of the unwanted plants, both to cropland and uncropped land.

If the crop plants tolerate the active ingredients less well, application techniques may be used in which the agents are sprayed from suitable equipment in such a manner that the leaves of sensitive crop plants are if possible not touched, and the agents reach the soil of the unwanted plants growing beneath the crop plants (post-directed, lay-by treatment).

Depending on the season and the growth stage of the plants, the application rates of active ingredient are from 0.1 to 15 kg/ha and more, the higher rates being particularly suitable for the total elimination of vegetation.

The influence of various representatives of 4H-3,1-benzoxazine derivatives according to the invention on the growth of unwanted plants is demonstrated in greenhouse experiments, in which prior art compounds were used for comparison purposes.

The vessels employed were plastic flowerpots having a volume of 300 cm³, and which were filled with a sandy loam containing about 1.5% humus. The seeds of the test plants (cf. Table 1) were sown shallow, and separately, according to species, or pregerminated young plants, cuttings or tubers of Cyperus esculentus were used.

Generally, the plants were grown to a height of 3 to 10 cm, depending on the growth shape, before being treated. The compounds were emulsified or suspended in water as vehicle, and sprayed through finely distributing nozzles onto the shoot parts of the plants and the soil not completely covered by plants. The pots were set up in the greenhouse-species from warmer areas at from 20° to 30° C., and species from moderate climates at 10° to 20° C. The experiments were run for from 2 to 4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The prior art active ingredients used for comparison purposes were 2-(3'-trifluoromethylphenyl)-4H-3,1-benzoxazin-4-one ($V_1$; U.S. Pat. No. 3,970,652) and 3-isopropyl-2,1,3-benzothiadiazin-4-one-2,2-dioxide ($V_2$; German Pat. No. 1,542,836).

TABLE 1

| List of plant names | |
|---|---|
| Botanical name | Abbreviation in tables |
| *Amaranthus retroflexus* | Amar. retrofl. |
| *Desmodium tortuosum* | Desmod. tort. |
| *Euphorbia geniculata* | Euph. genic. |
| *Matricaria spp.* | Matric. spp. |
| *Mercurialis annua* | Mercur. annua |
| *Triticum aestivum* | Tritic. aest. |
| *Zea mays* | — |
| *Solanum nigrum* | |
| *Chenopodium album* | |

TABLE 2

Selective herbicidal action of 4H—3,1-benzoxazine derivatives in cereals; postemergence treatment in the greenhouse

| Active ingredient no. | Appln. rate (kg a.i./ha) | Tritic. aest. | Zea mays | Amar. retrofl. | Desmod. tort. | Euph. genic. | Matric. spp. | Mercur. annua |
|---|---|---|---|---|---|---|---|---|
| 1 | 0.25 | 0 | 0 | — | 80 | 100 | 100 | 100 |
|   | 0.5 | 0 | 0 | 85 | 100 | 100 | 100 | 100 |
| 2 | 0.25 | 0 | 2 | — | 68 | 99 | 100 | 100 |
|   | 0.5 | 0 | 8 | 50 | 100 | 100 | 100 | 100 |
| $V_1$ | 0.25 | 0 | 0 | — | 8 | 2 | 65 | 68 |
|   | 0.5 | 0 | 0 | 11 | 8 | 19 | 88 | 80 |
| $V_2$ | 0.25 | 0 | 0 | — | 0 | 0 | 100 | 5 |
|   | 0.5 | 0 | 0 | 22 | 0 | 0 | 100 | 5 |

TABLE 3

Selective herbicidal action of 4H—3,1-benzoxazine derivatives; postemergence treatment in the greenhouse

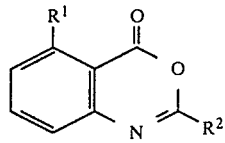

| Active ingredient no. | $R^1$ | $R^2$ | Appln. rate (kg a.i./ha) | Triticum aestivum | Chenopodium album |
|---|---|---|---|---|---|
| 14 | H | (3-substituted phenyl with O—CCl=CHCl) | 0.5 | 0 | 100 |
| 34 | H | (methylthiophene) | 0.5 | 0 | 98 |
| 68 | Cl | (methylthiophene) | 1.0 | 0 | 98 |

TABLE 3-continued

Selective herbicidal action of 4H—3,1-benzoxazine derivatives; postemergence treatment in the greenhouse

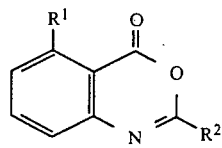

| Active ingredient no. | R¹ | R² | Appln. rate (kg a.i./ha) | Triticum aestivum | Chenopodium album |
|---|---|---|---|---|---|
| 61 | Cl | —⟨benzene⟩—CFCl₂ | 1.0 | 0 | 100 |
| 69 | F | —⟨thiophene S⟩ | 0.5 | 0 | 100 |
| 4 | H | —⟨benzene⟩—CF₂Cl | 0.5 | 0 | 98 |
| 73 | Cl | —⟨benzene⟩—CF₂Cl | 0.5 | 0 | 98 |
| 87 | F | —⟨benzene⟩—CF₂Cl | 0.5 | 0 | 90 |

TABLE 4

Selective control of broadleaved weeds in Indian corn and cereals with 4H—3,1-benzoxazine derivatives; postemergence treatment in the greenhouse

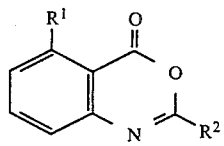

| Active ingredient no. | R¹ | R² | Appln. rate (kg a.i./ha) | Triticum aestivum | Zea mays | Desmodium tortuosum | Solanum nigrum |
|---|---|---|---|---|---|---|---|
| 52 | F | —⟨benzene⟩—CF₃ | 0.5 | 0 | 5 | 100 | 100 |
| 50 | Cl | —⟨benzene⟩—CF₃ | 0.5 | 0 | 0 | 100 | 100 |

TABLE 4-continued

Selective control of broadleaved weeds in Indian corn and cereals with 4H—3,1-benzoxazine derivatives; postemergence treatment in the greenhouse

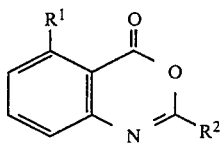

| Active ingredient no. | R¹ | R² | Appln. rate (kg a.i./ha) | Triticum aestivum | Zea mays | Desmodium tortuosum | Solanum nigrum |
|---|---|---|---|---|---|---|---|
| 5 | H | (phenyl)-CFCl₂ | 0.5 | 0 | — | — | 100 |
| 73 | Cl | (phenyl)-CF₂Cl | 0.5 | 0 | 0 | 100 | — |
| 87 | F | (phenyl)-CF₂Cl | 0.5 | 0 | 0 | 100 | — |

In view of the good tolerance of the active ingredients and the many application methods possible, the agents according to the invention, or mixtures containing them, may be used not only on the crop plants listed in Table 1, but also in a much larger range of crops for removing unwanted plants.

The following crop plants may be mentioned by way of example:

| Botanical name | Common name |
|---|---|
| *Allium cepa* | onions |
| *Ananas comosus* | pineapples |
| *Arachis hypogaea* | peanuts (groundnuts) |
| *Asparagus officinalis* | asparagus |
| *Avena sativa* | oats |
| *Beta vulgaris* spp. *altissima* | sugarbeets |
| *Beta vulgaris* spp. *rapa* | fodder beets |
| *Beta vulgaris* spp. *esculenta* | table beets, red beets |
| *Brassica napus* var. *napus* | rape |
| *Brassica napus* var. *napobrassica* | |
| *Brassica napus* var. *rapa* | turnips |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *Citrus maxima* | grapefruits |
| *Citrus reticulata* | |
| *Citrus sinensis* | orange trees |
| *Coffea arabica* (*Coffea canephora*, *Coffea liberica*) | coffee plants |
| *Cucumis melo* | melons |
| *Cucumis sativus* | cucumbers |
| *Cynodon dactylon* | Bermudagrass in turf and lawns |
| *Daucus carota* | carrots |
| *Elais guineensis* | oil palms |
| *Fragaria vesca* | strawberries |
| *Glycine max* | soybeans |
| *Gossypium hirsutum* (*Gossypium arboreum* *Gossypium herbaceum* *Gossypium vitifolium*) | cotton |
| *Helianthus annuus* | Sunflowers |
| *Helianthus tuberosus* | |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lactuca sativa* | lettuce |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Mentha piperita* | peppermint |
| *Musa* spp. | banana plants |
| *Nicothiana tabacum* (*N. rustica*) | tobacco |
| *Olea europaea* | olive trees |
| *Oryza sativa* | rice |
| *Panicum miliaceum* | |
| *Phaseolus lunatus* | limabeans |
| *Phaseolus mungo* | mungbeans |
| *Phaseolus vulgaris* | snapbeans, green beans, dry beans |
| *Pennisetum glaucum* | |
| *Petroselinum crispum* spp. *tuberosum* | parsley |
| *Picea abies* | Norway spruce |
| *Abies alba* | fir trees |
| *Pinus* spp. | pine trees |
| *Pisum sativum* | English peas |
| *Prunus avium* | cherry trees |

| Botanical name | Common name |
| --- | --- |
| *Prunus domestica* | plum trees |
| *Prunus dulcis* | almond trees |
| *Prunus persica* | peach trees |
| *Pyrus communis* | pear trees |
| *Ribes sylvestre* | redcurrants |
| *Ribes uva-crispa* | gooseberries |
| *Ricinus communis* | castor-oil plants |
| *Saccharum officinarum* | sugar cane |
| *Secale cereale* | rye |
| *Sesamum indicum* | sesame |
| *Solanum tuberosum* | Irish potatoes |
| *Sorghum bicolor (s. vulgare)* | sorghum |
| *Sorghum dochna* | |
| *Spinacia oleracea* | spinach |
| *Theobroma cacao* | cacao plants |
| *Trifolium pratense* | red clover |
| *Triticum aestivum* | wheat |
| *Vaccinium corymbosum* | blueberries |
| *Vaccinium vitis-idaea* | cranberries |
| *Vicia faba* | tick beans |
| *Vigna sinensis (V. unguiculata)* | cow peas |
| *Vitis vinifera* | grapes |
| *Zea mays* | Indian corn, sweet corn, maize |

To increase the spectrum of action and to achieve synergistic effects, the 4H-3,1-benzoxazine derivatives of the formula I may be mixed among themselves or mixed and applied together with numerous representatives of other herbicidal or growth-regulating active ingredient groups. Examples of suitable mixture components are diazines, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc. A number of active ingredients which, when combined with the new compounds, give mixtures useful for widely varying applications are given below by way of example:

5-amino-4-chloro-2-phenyl-3(2H)-pyridazinone
5-amino-4-bromo-2-phenyl-3(2H)-pyridazinone
5-amino-4-chloro-2-cyclohexyl-3(2H)-pyridazinone
5-amino-4-bromo-2-cyclohexyl-3(2H)-pyridazinone
5-methylamino-4-chloro-2-(3-trifluoromethylphenyl)-3(2H)-pyridazinone
5-methylamino-4-chloro-2-(3-α,α,β,β-tetrafluoroethoxyphenyl)-3(2H)-pyridazinone
5-dimethylamino-4-chloro-2-phenyl-3(2H)-pyridazinone
4,5-dimethoxy-2-phenyl-3(2H)-pyridazinone
4,5-dimethoxy-2-cyclohexyl-3(2H)-pyridazinone
4,5-dimethoxy-2-(3-trifluoromethylphenyl)-3(2H)-pyridazinone
5-methoxy-4-chloro-2-(3-trifluoromethylphenyl)-3(2H)-pyridazinone
5-amino-4-bromo-2(3-methylphenyl)-3(2H)-pyridazinone
4,5-dimethoxy-2-(3-α,α,β-trifluoro-β-bromoethoxyphenyl)-3-(2H)-pyridazinone
3-(1-methylethyl)-1H-2,1,3-benzothiadiazin-4(3H)-one-2,2-dioxide and salts
3-(1-methylethyl)-8-chloro-1H-2,1,3-benzothiadiazin-4(3H)-one-2,2-dioxide and salts
3-(1-methylethyl)-8-fluoro-1H-2,1,3-benzothiadiazin-4(3H)-one-2,2-dioxide and salts
3-(1-methylethyl)-8-methyl-1H-2,1,3-benzothiadiazin-4(3H)-one-2,2-dioxide and salts
1-methoxymethyl-3-(1-methylethyl)-2,1,3-benzothiadiazin-4(3H)-one-2,2-dioxide
1-mthoxymethyl-8-chloro-3-(1-methylethyl)-2,1,3-benzothiadiazin-4(3H)-one-2,2-dioxide
1-methoxymethyl-8-fluoro-3-(1-methylethyl)-2,1,3-benzothiadiazin-4(3H)-one-2,2-dioxide
1-cyano-8-chloro-3-(1-methylethyl)-2,1,3-benzothiadiazin-4(3H)-one-2,2-dioxide
1-cyano-8-fluoro-3-(1-methylethyl)-2,1,3-benzothiadiazin-4(3H)-one-2,2-dioxide
1-cyano-8-methyl-3-(1-methylethyl)-2,1,3-benzothiadiazin-4(3H)-one-2,2-dioxide
1-cyano-3-(1-methylethyl)-2,1,3-benzothiadiazin-4(3H)-one-2,2-dioxide
1-azidomethyl-3-(1-methylethyl)-2,1,3-benzothiadiazin-4(3H)-one-2,2-dioxide
3-(1-methylethyl)-1H-pyridino-[3,2-e]-2,1,3-thiadiazin-(4)-one-2,2-dioxide
N-(1-ethylpropyl)-2,6-dinitro-3,4-dimethylaniline
N-(1-methylethyl)-N-ethyl-2,6-dinitro-4-trifluoromethylaniline
N-n-propyl-N-β-chloroethyl-2,6-dinitro-4-trifluoromethylaniline
N-n-propyl-N-cyclopropylmethyl-2,6-dinitro-4-trifluoromethylaniline
N-bis-(n-propyl)-2,6-dinitro-3-amino-4-trifluoromethylaniline
N-bis-(n-propyl)-2,6-dinitro-4-methylaniline
N-bis-(n-propyl)-2,6-dinitro-4-methylsulfonylaniline
N-bis-(n-propyl)-2,6-dinitro-4-aminosulfonylaniline
bis-(β-chloroethyl)-2,6-dinitro-4-methylaniline
N-ethyl-N-(2-methylallyl)-2,6-dinitro-4-trifluoromethylaniline
3,4-dichlorobenzyl N-methylcarbamate
2,6-di-tert.butyl-4-methylphenyl N-methylcarbamate
isopropyl N-phenylcarbamate
3-methoxyprop-2-yl N-3-fluorophenylcarbamate
isopropyl N-3-chlorophenylcarbamate
but-1-yn-3-yl N-3-chlorophenylcarbamate
4-chlorobut-2-yn-1-yl N-3-chlorophenylcarbamate
methyl N-3,4-dichlorophenylcarbamate
methyl N-(4-aminobenzenesulfonyl)-carbamate
O-(N-phenylcarbamoyl)-propanone oxime
N-ethyl-2-(phenylcarbamoyl)-oxypropionic acid amide
3'-N-isopropylcarbamoyloxypropionanilide
ethyl-N-(3-(N'-phenylcarbamoyloxy)-phenyl)-carbamate
methyl-N-(3-(N'-methyl-N'-phenylcarbamoyloxy)-phenyl)-carbamate
isopropyl-N-(3-(N'-ethyl-N'-phenylcarbamoyloxy)-phenyl)-carbamate
methyl-N-(3-(N'-3-methylphenylcarbamoyloxy)-phenyl)-carbamate
methyl-N-(3-(N'-4-fluorophenylcarbamoyloxy)-phenyl)-carbamate
methyl-N-(3-(N'-3-chloro-4-fluorophenylcarbamoyloxy)-phenyl)-carbamate
ethyl-N-[3-N'-(3-chloro-4-fluorophenylcarbamoxyloxy)-phenyl]-carbamate
ethyl-N-[3-N'-(3,4-difluorophenylcarbamoyloxy)-phenyl]-carbamate
methyl-N-[3-(N'-3,4-difluorophenylcarbamoyloxy)-phenyl]-carbamate
methyl N-3-(4'-fluorophenoxycarbonylamino)-phenyl-carbamate
ethyl N-3-(2'-methylphenoxycarbonylamino)-phenyl-carbamate
methyl N-3-(4'-fluorophenoxycarbonylamino)-phenyl-thiolcarbamate methyl N-3-(2',4',5'-trimethylphenoxycarbonylamino)-phenylthiolcarbamate
methyl N-3-(phenoxycarbonylamino)-phenylthiolcarbamate
p-chlorobenzyl N,N-diethylthiolcarbamate
ethyl N,N-di-n-propylthiolcarbamate
n-propyl N,N-di-n-propylthiolcarbamate
2,3-dichloroallyl N,N-diisopropylthiolcarbamate
2,3,3-trichloroallyl N,N-diisopropylthiolcarbamate
3-methyl-5-isoxazolylmethyl N,N-diisopropylthiolcarbamate
3-ethyl-5-isoxazolylmethyl N,N-diisopropylthiolcarbamate
ethyl N,N-di-sec.-butylthiolcarbamate
benzyl N,N-di-sec.-butylthiolcarbamate
ethyl N-ethyl-N-cyclohexylthiolcarbamate
ethyl N-ethyl-N-bicyclo-[2.1.1]-heptylthiolcarbamate
S-(2,3-dichloroallyl)-(2,2,4-trimethylazetidine)-1-carbothiolate
S-(2,3,3-trichloroallyl)-(2,2,4-trimethylazetidine)-1-carbothiolate
S-ethylhexahydro-1-H-azepine-1-carbothiolate
S-benzyl-(3-methylhexahydro-1-H-azepine-1)-carbothiolate
S-benzyl-(2,3-dimethylhexahydro-1-H-azepine-1)-carbothiolate
S-ethyl-(3-methylhexahydro-1-H-azepine-1)-carbothiolate
n-propyl N-ethyl-N-n-butylthiolcarbamate
2-chloroallyl N,N-dimethyldithiocarbamate
N-methyldithiocarbamic acid, sodium salt
trichloroacetic acid, sodium salt
α,α-dichloropropionic acid, sodium salt
α,α-dichlorobutyric acid, sodium salt
α,α-β,β-tetrafluoropropionic acid, sodium salt
α-methyl-α,β-dichloropropionic acid, sodium salt
methyl α-chloro-β-(4-chlorophenyl)-propionate
methyl α,β-dichloro-β-phenylpropionate
benzamido oxyacetic acid
2,3,5-triiodobenzoic acid (salts, esters, amides)
2,3,6-trichlorobenzoic acid (salts, esters, amides)
2,3,5,6-tetrachlorobenzoic acid (salts, esters, amides)
2-methoxy-3,6-dichlorobenzoic acid (salts, esters, amides)
2-methoxy-3,5,6-trichlorobenzoic acid (salts, esters, amides)
3-amino-2,5,6-trichlorobenzoic acid (salts, esters, amides)
O,S-dimethyltetrachlorothioterephthalate
dimethyl-2,3,5,6-tetrachloroterephthalate
disodium 3,6-endoxohexahydrophthalate
4-amino-3,5,6-trichloropicolinic acid (salts)
ethyl 2-cyano-3-(N-methyl-N-phenyl)-aminoacrylate
isobutyl 2-[4-(4'-chlorophenoxy)-phenoxy]-propionate
methyl 2-[4-(2',4'-dichlorophenoxy)-phenoxy]-propionate
methyl 2-[4-(4'-trifluoromethylphenoxy)-phenoxy]-propionate
2-[4-(2'-chloro-4'-trifluorophenoxy)-phenoxy]-propionic acid, sodium salt,
2-[4-(3',5'-dichloropyridyl-2-oxy)-phenoxy]-propionic acid, sodium salt
ethyl 2-(N-benzoyl-3,4-dichlorophenylamino)-propionate
methyl 2-(N-benzoyl-3-chloro-4-fluorophenylamino)-propionate
isopropyl 2-(N-benzoyl-3-chloro-4-fluorophenylamino)-propionate
ethyl 4-(4'-trifluoromethylphenoxy)-pentene-2-carboxylate
2-chloro-4-ethylamino-6-isopropylamino-1,3,5-triazine
2-chloro-4-ethylamino-6-(amino-2'-propionitrile)-1,3,5-triazine
2-chloro-4-ethylamino-6-(2-methoxypropyl)-2-amino-1,3,5-triazine
2-chloro-4-ethylamino-6-butyn-1-yl-2-amino-1,3,5-triazine
2-chloro-4,6-bisethylamino-1,3,5-triazine
2-chloro-4,6-bisisopropylamino-1,3,5-triazine
2-chloro-4-isopropylamino-6-cyclopropylamino-1,3,5-triazine
2-azido-4-methylamino-6-isopropylamino-1,3,5-triazine
2-methylthio-4-ethylamino-6-isopropylamino-1,3,5-triazine
2-methylthio-4-ethylamino-6-tert.butylamino-1,3,5-triazine
2-methylthio-4,6-bisethylamino-1,3,5-triazine
2-methylthio-4,6-bisisopropylamino-1,3,5-triazine
2-methoxy-4-ethylamino-6-isopropylamino-1,3,5-triazine
2-methoxy-4,6-bisethylamino-1,3,5-triazine
2-methoxy-4,6-bisisopropylamino-1,3,5-triazine
4-amino-6-tert.butyl-3-methylthio-4,5-dihydro-1,2,4-triazin-5-one
4-amino-6-phenyl-3-methyl-4,5-dihydro-1,2,4-triazin-5-one
4-isobutylidenamino-6-tert.butyl-3-methylthio-4,5-dihydro-1,2,4-triazin-5-one
1-methyl-3-cyclohexyl-6-dimethylamino-1,3,5-triazin-2,4-dione
3-tert.butyl-5-chloro-6-methyluracil
3-tert.butyl-5-bromo-6-methyluracil
3-isopropyl-5-bromo-6-methyluracil
3-sec.butyl-5-bromo-6-methyluracil
3-(2-tetrahydropyranyl)-5-chloro-6-methyluracil
3-(2-tetrahydropyranyl)-5,6-trimethyleneuracil 3-cyclohexyl-5,6-trimethyleneuracil
2-methyl-4-(3'-trifluoromethylphenyl)-tetrahydro-1,2,4-oxadiazine-3,5-dione
2-methyl-4-(4'-fluorophenyl)-tetrahydro-1,2,4-oxadiazine-3,5-dione
3-amino-1,2,4-triazole
1-allyloxy-1-(4-bromophenyl)-2-[1',2',4'-triazolyl-(1')]-ethane (salts)
1-(4-chlorophenoxy)-3,3-dimethyl-1-(1H-1,2,3-triazol-1-yl)-butan-2-one
N,N-diallylchloroacetamide
N-isopropyl-2-chloroacetanilide
N-(but-1-yn-3-yl)-2-chloroacetanilide
2-methyl-6-ethyl-N-propargyl-2-chloroacetanilide
2-methyl-6-ethyl-N-ethoxymethyl-2-chloroacetanilide
2-methyl-6-ethyl-N-(2-methoxy-1-methylethyl)-2-chloroacetanilide
2-methyl-6-ethyl-N-(isopropoxycarbonylethyl)-2-chloroacetanilide
2-methyl-6-ethyl-N-(4-methoxypyrazol-B 1-yl-methyl)-2-chloroacetanilide
2-methyl-6-ethyl-N-(pyrazol-1-yl-methyl)-2-chloroacetanilide
2,6-dimethyl-N-(pyrazon-1-yl-methyl)-2-chloroacetanilide
2,6-dimethyl-N-(4-methylpyrazol-1-yl-methyl)-2-chloro-acetanilide
2,6-dimethyl-N-(1,2,4-triazol-1-yl-methyl)-2-chloroacetanilide 2,6-dimethyl-N-(3,5-dimethylpyrazol-1-yl-methyl)-2-chloroacetanilide
2,6-dimethyl-N-(1,3-dioxolan-2-yl-methyl)-2-chloroacetanilide
2,6-dimethyl-N-(2-methoxyethyl)-2-chloroacetanilide
2,6-dimethyl-N-isobutoxymethyl-2-chloroacetanilide
2,6-diethyl-N-methoxymethyl-2-chloroacetanilide
2,6-diethyl-N-n-butoxymethyl-2-chloroacetanilide
2,6-diethyl-N-ethoxycarbonylmethyl-2-chloroacetanilide
2,3,6-trimethyl-N-(pyrazol-1-yl-methyl)-2-chloroacetanilide
2,3-dimethyl-N-isopropyl-2-chloroacetanilide
2-(2-methyl-4-chlorophenoxy)-N-methoxyacetamide
2-(α-naphthoxy)-N,N-diethylpropionamide
2,2-diphenyl-N,N-dimethylacetamide
N-benzyl-N-isopropyl-trimethylacetamide
α-(3,4,5-tribromopyrazol-1-yl)-N,N-dimethylpropionamide
N-(1,1-dimethylpropynyl)-3,5-dichlorobenzamide
N-1-naphthylphthalamic acid
propionic acid 3,4-dichloroanilide
cyclopropanecarboxylic acid 3,4-dichloroanilide
methacrylic acid 3,4-dichloroanilide
2-methylpentanecarboxylic acid 3,4-dichloroanilide
5-acetamido-2,4-dimethyl-trifluoromethane-sulfanilide
5-acetamido-4-methyl-trifluoromethanesulfanilide
2-propionylamino-4-methyl-5-chlorothiazole
O-(methylsulfonyl)-glycolic acid N-ethoxymethyl-2,6-dimethylanilide
O-(methylaminosulfonyl)-glycolic acid N-isopropylanilide
O-(isopropylaminosulfonyl)-glycolic acid N-but-1-yn-3-yl-anilide
O-(methylaminosulfonyl)-glycolic acid hexamethyleneamide
2,6-dichlorothiobenzamide
2,6-dichlorobenzonitrile
3,5-dibromo-4-hydroxybenzonitrile (salts)
3,5-diiodo-4-hydroxybenzonitrile (salts)
3,5-dibromo-4-hydroxy-O-2,4-dinitrophenylbenzaldoxime (salts)
3,5-dibromo-4-hydroxy-O-2-cyano-4-nitrophenylbenzaldoxime (salts)
pentachlorophenol, sodium salt
2,4-dichlorophenyl-4'-nitrophenyl ether
2,4,6-trichlorophenyl-4'-nitrophenyl ether
2-fluoro-4,6-dichlorophenyl-4'-nitrophenyl ether
2-chloro-4-trifluoromethylphenyl-4'-nitrophenyl ether
2,4'-dinitro-4-trifluoromethyl-diphenyl ether
2,4-dichlorophenyl-3'-methoxy-4'-nitro-phenyl ether
2-chloro-4-trifluoromethylphenyl-3'-ethoxy-4'-nitrophenyl ether
2-chloro-4-trifluoromethylphenyl-3'-carboxy-4'-nitrophenyl ether (salts)
2-chloro-4-trifluoromethylphenyl-3'-ethoxycarbonyl-4'-nitro-phenyl ether
2-chloro-4-trifluoromethylphenyl-3'-(2-fluoroethoxy)-4'-nitro-phenyl ether
2-chloro-4-trifluoromethylphenyl-3'-ethoxycarbonylmethylthio-4'-nitro-phenyl ether
2-chloro-4-trifluoromethylphenyl-3'-methoxycarbonyl-4'-nitro-phenyl ether
2,4,6-trichlorophenyl-3-ethoxycarbonyl-methylthio-4'-nitro-phenyl ether
2,4-dichlorophenyl-3'-methoxycarbonyl-4'-nitro-phenyl ether
2,4-dichlorophenyl-3'-carboxy-4'-nitro-phenyl ether
2-(3,4-dichlorophenyl)-4-methyl-1,2,4-oxadiazolidine-3,5-dione
2-(3-tert.butylcarbamoyloxyphenyl)-4-methyl-1,2,4-oxadiazolidine-3,5-dione
2-(3-isopropylcarbamoyloxyphenyl)-4-methyl-1,2,4-oxadiazolidine-3,5-dione
2-phenyl-3,1-benzoxazinone-(4)
(4-bromophenyl)-3,4,5,9,10-pentaazatetracyclo-[5,4,1,0$^{2,6}$,0,$^{8,11}$]-dodeca-3,9-diene
2-ethoxy-2,3-dihydro-3,3-dimethyl-5-benzofuranylmethane sulfonate
2-ethoxy-2,3-dihydro-3,3-dimethyl-5-benzofuranyl-dimethylaminosulfate
2-ethoxy-2,3-dihydro-3,3-dimethyl-5-benzofuranyl-(N-methyl-N-acetyl)-aminosulfonate
3,4-dichloro-1,2-benzisothiazole
N-4-chlorophenyl-allylsuccinimide
2-methyl-4,6-dinitrophenol (salts, esters)
2-sec.butyl-4,6-dinitrophenol (salts, esters)
2-sec.butyl-4,6-dinitrophenol acetate
2-tert.butyl-4,6-dinitrophenol acetate
2-tert.butyl-4,6-dinitrophenol (salts)
2-tert.butyl-5-methyl-4,6-dinitrophenol (salts)
2-tert.butyl-5-methyl-4,6-dinitrophenol acetate
2-sec.amyl-4,6-dinitrophenol (salts, esters)
1-(α,α-dimethylbenzyl)-3-(4-methylphenyl)-urea
1-phenyl-3-(2-methylcyclohexyl)-urea
1-phenyl-1-benzoyl-3,3-dimethylurea
1-(4-chlorophenyl)-1-benzoyl-3,3-dimethylurea
1-(4-chlorophenyl)-3,3-dimethylurea
1-(4-chlorophenyl)-3-methyl-3-but-1-yn-3-yl-urea
1-(3,4-dichlorophenyl)-3,3-dimethylurea
1-(3,4-dichlorophenyl)-1-benzoyl-3,3-dimethylurea
1-(3,4-dichlorophenyl)-3-methyl-3-n.butylurea
1-(4-isopropylphenyl)-3,3-dimethylurea
1-(3-trifluoromethylphenyl)-3,3-dimethylurea
1-(α,α,β,β-tetrafluoroethoxyphenyl)-3,3-dimethylurea
1-(3-tert.butylcarbamoyloxyphenyl)-3,3-dimethylurea
1-(3-chloro-4-methylphenyl)-3,3-dimethylurea
1-(3-chloro-4-methoxyphenyl)-3,3-dimethylurea
1-(3,5-dichloro-4-methoxyphenyl)-3,3-dimethylurea
1-[4-(4'-chlorophenoxy)-phenyl]-3,3-dimethylurea
1-[4-(4'-methoxyphenoxy)-phenyl]-3,3-dimethylurea
1-cyclooctyl-3,3-dimethylurea
1-(hexahydro-4,7-methanoindan-5-yl)-3,3-dimethylurea
1-[1- or 2-(3a,4,5,7,7a-hexahydro)-4,7-methanoindanyl]-3,3-dimethylurea
1-(4-fluorophenyl)-3-carboxymethoxy-3-methylurea
1-phenyl-3-methyl-3-methoxyurea
1-(4-chlorophenyl)-3-methyl-3-methoxyurea
1-(4-bromophenyl)-3-methyl-3-methoxyurea
1-(3,4-dichlorophenyl)-3-methyl-3-methoxyurea
1-(3-chloro-4-bromophenyl)-3-methyl-3-methoxyurea
1-(3-chloro-4-isopropylphenyl)-3-methyl-3-methoxyurea
1-(3-chloro-4-methoxyphenyl)-3-methyl-3-methoxyurea
1-(3-tert.butylphenyl)-3-methyl-3-methoxyurea
1-(2-benzthiazolyl)-1,3-dimethylurea
1-(2-benzthiazolyl)-3-methylurea
1-(5-trifluoromethyl-1,3,4-thiadiazolyl)-1,3-dimethylurea
imidazolidin-2-one-1-carboxylic acid isobutylamide
1,2-dimethyl-3,5-diphenylpyrazolium-methylsulfate
1,2,4-trimethyl-3,5-diphenylpyrazolium-methylsulfate
1,2-dimethyl-4-bromo-3,5-diphenylpyrazolium-methylsulfate 1,3-dimethyl-4-(3,4-dichlorobenzoyl)-5-(4-methyl-
 phenylsulfonyloxy)-pyrazole
1-acetyl-3-anilino-4-methoxycarbonyl-5-methyl-
 pyrazole
3-anilino-4-methoxycarbonyl-5-methylpyrazole
3-tert-butylamino-4-methoxycarbonyl-5-methyl-
 pyrazole
2,3,5-trichloropyridinol-(4)
1-methyl-3-phenyl-5-(3'-trifluoromethylphenyl)-pyri-
 done-(4)
1-methyl-4-phenylpyridinium chloride
1,1-dimethylpyridinium chloride
3-phenyl-4-hydroxy-6-chloropyridazine
1,1'-dimethyl-4,4'-dipyridylium-di(methylsulfate)
1,1'-di-(3,5-dimethylmorpholine-carbonylmethyl)-4,4'-
 dipyridylium dichloride
1,1'-ethylene-2,2'-dipyridylium dibromide
3-[1-(N-ethoxyamino)-propylidene]-6-ethyl-3,4-dihy-
 dro-2H-pyran-2,4-dione
3-[1-(N-allyloxyamino)-propylidene]-6-ethyl-3,4-dihy-
 dro-2H-pyran-2,4-dione
2-[1-(N-allyloxyamino)-propylidene]-5,5-dimethylcy-
 clohexane-1,3-dione (salts)
2-[1-(N-allyloxyamino-butylidene]-5,5-dimethylcy-
 clohexane-1,3-dione (salts)
2-[1-(N-allyloxyamino-butylidene]-5,5-dimethyl-4-
 methoxycarbonyl-cyclohexane-1,3-dione (salts)
2-chlorophenoxyacetic acid (salts, esters, amides)
4-chlorophenoxyacetic acid (salts, esters, amides)
2,4-dichlorophenoxyacetic acid (salts, esters, amides)
2,4,5-trichlorophenoxyacetic acid (salts, esters, amides)
2-methyl-4-chlorophenoxyacetic acid (salts, esters, am-
 ides)
3,5,6-trichloro-2-pyridinyl-oxyacetic acid (salts, esters,
 amides)
methyl α-naphthoxyacetate
ethyl 2-[4-(5'-bromopyridyl-2-oxy)-phenoxy]-propion-
 ate
ethyl 2-[4-(5'-iodopyridyl-2-oxy)-phenoxy]-propionate
n-butyl 2-[4-(5'-iodopyridyl-2-oxy)-phenoxy]-propion-
 ate
2-(2-methylphenoxy)-propionic acid (salts, esters, am-
 ides)
2-(4-chlorophenoxy)-propionic acid (salts, esters, am-
 ides)
2-(2,4-dichlorophenoxy)-propionic acid (salts, esters,
 amides)
2-(2,4,5-trichlorophenoxy)-propionic acid (salts, esters,
 amides)
2-(2-methyl-4-chlorophenoxy)-propionic acid (salts,
 esters, amides)
2-[4-(4'-chlorophenoxymethyl)-phenoxy]-propionate
4-(2,4-dichlorophenoxy)-butyric acid (salts, esters, am-
 ides)
4-(2-methyl-4-chlorophenoxy)-butyric acid (salts, es-
 ters, amides)
cyclohexyl-3-(2,4-dichlorophenoxy)-acrylate
9-hydroxyfluorenecarboxylic acid-(9) (salts, esters)
2,3,6-trichlorophenylacetic acid (salts, esters)
4-chloro-2-oxobenzothiazolin-3-yl-acetic acid (salts,
 esters)
2-[1-(N-ethoxamino)-butylidene]-5-(2-ethylthiopropyl)-
 3-hydroxycyclohex-2-en-1-one (salts)
2-[1-(N-ethoxamino)-butylidene]-5-(2-phenylthio-
 propyl)-3-hydroxycyclohex-2-en-1-one (salts)
gibelleric acid (salts)
disodium methylarsonate
monosodium salt of methylarsonic acid N-phosphonomethyl-glycine (salts)
N,N-bis-(phosphonomethyl)-glycine (salts)
2-chloroethyl 2-chloroethanephosphonate
ammonium-ethyl-carbamoyl-phosphonate
di-n-butyl-1-n-butylamino-cyclohexyl-phosphonate
trithiobutylphosphite
O,O-diisopropyl-5-(2-benzosulfonylaminoethyl)-phos-
 phorodithionate
2,3-dihydro-5,6-dimethyl-1,4-dithiin-1,1,4,4-tetraoxide
5-tert.butyl-3-(2,4-dichloro-5-isopropoxyphenyl)-1,3,4-
 oxadiazolone-(2)
4,5-dichloro-2-trifluoromethylbenzimidazole (salts)
1,2,3,6-tetrahydropyridazine-3,6-dione (salts)
succinic acid mono-N-dimethylhydrazide (salts)
(2-chloroethyl)-trimethylammonium chloride
(2-methyl-4-phenylsulfonyl)-trifluoromethanesulfone
 anilide
1,1-dimethyl-4,6-diisopropyl-5-indanyl ethyl ketone
2-[1-(2,5-dimethylphenyl)-ethylsulfonyl]-pyridine-N-
 oxide
sodium chlorate
ammonium thiocyanate
calcium cyanamide It may also be useful to apply the compounds accord-
ing to the invention in admixture with other herbicides
or other crop protection agents, e.g., agents for combat-
ing pests or phytopathogenic fungi or bacteria. The
compounds may also be mixed with solutions of mineral
matters used to remedy nutritional or trace element
deficiencies. To initiate the herbicidal action, wetting
agents, spreader-stickers and non-phytotoxic oils and oil
concentrates may be added.

We claim:

1. A 4H-3,1-benzoxazine derivative of the formula

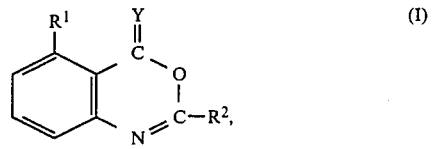

where
 $R^1$ is halogen,
 Y is oxygen or sulfur and
 $R^2$ is phenyl which is monosubstituted by haloalkyl of
  up to 3 carbon atoms.
2. 5-Chloro-2-(3'-trifluoromethyl-phenyl)-4H-3,1-
 benzoxazin-4-one.
3. 5-Fluoro-2-(3'-trifluoromethyl-phenyl)-4H-3,1-
 benzoxazin-4-one.
4. A herbicidal composition comprising a carrier
and/or diluent and a herbicidally effective amount of a
compound of the formula

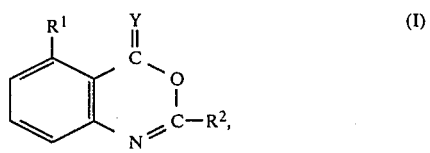

where
 $R^1$ is halogen,
 Y is oxygen or sulfur and
 $R^2$ is phenyl which is monosubstituted by haloalkyl of
  up to 3 carbon atoms.

5. A herbicidal composition as set forth in claim 4 wherein in the compound of the formula I, $R^1$ is halogen, Y is oxygen and $R^2$ is phenyl monosubstituted by haloalkyl of up to 3 carbon atoms.

6. A herbicidal composition as set forth in claim 4 wherein the compound of the formula I is 5-chloro-2-(3'-trifluoromethyl-phenyl)-4H-3,1-benzoxazin-4-one.

7. A herbicidal composition as set forth in claim 4 wherein the compound of the formula I is 5-fluoro-2-(3'-trifluoromethyl-phenyl)-4H-3,1-benzoxazin-4-one.

8. A herbicidal composition as set forth in claim 4, wherein the compound of the formula I is 5-chloro-2-(3'-fluorodichloromethyl-phenyl)-4H-3,1-benzoxazin-4-one.

9. A herbicidal composition as set forth in claim 4, wherein the compound of the formula I is 5-fluoro-2-(3'-difluorochloromethyl-phenyl)-4H-3,1-benzoxazin-4-one.

10. A process for the control of unwanted plant growth, wherein a herbicide is used which contains at least one 4H-3,1-benzoxazine derivative of the formula I as set forth in claim 1.

11. A process for the control of unwanted plant growth as set forth in claim 10, wherein the compound of the formula I is 5-chloro-2-(3'-trifluoromethyl-phenyl)-4H-3,1-benzoxazin-4-one.

12. A process for the control of unwanted plant growth as set forth in claim 10, wherein the compound of the formula I is 5-fluoro2-(3'-trifluoromethyl-phenyl)-4H-3,1-benzoxazin-4-one.

13. A process for the control of unwanted plant growth as set forth in claim 10, wherein the compound of the formula I is 5-chloro-2-(3'-fluorodichloromethyl-phenyl)-4H-3,1-benzoxazin-4-one.

14. A process for the control of unwanted plant growth as set forth in claim 10, wherein the compound of the formula I is 5-fluoro-2-(3'-difluorochloromethyl-phenyl)-4H-3,1-benzoxazin-4-one.

* * * * *